United States Patent
Mansour et al.

(10) Patent No.: US 11,259,710 B2
(45) Date of Patent: Mar. 1, 2022

(54) SYSTEM AND METHOD FOR REMOTE MEASUREMENTS OF VITAL SIGNS

(71) Applicants: Mitsubishi Electric Research Laboratories, Inc., Cambridge, MA (US); Mitsubishi Electric Corporation, Tokyo (JP)

(72) Inventors: Hassan Mansour, Boston, MA (US); Tim Marks, Newton, MA (US); Ewa Nowara, Houston, TX (US); Yudai Nakamura, Tokyo (JP); Ashok Veeraraghavan, Houston, TX (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 456 days.

(21) Appl. No.: 16/167,668

(22) Filed: Oct. 23, 2018

(65) Prior Publication Data

US 2019/0350471 A1    Nov. 21, 2019

Related U.S. Application Data

(60) Provisional application No. 62/672,433, filed on May 16, 2018.

(51) Int. Cl.
*A61B 5/024*    (2006.01)
*A61B 5/00*    (2006.01)
(Continued)

(52) U.S. Cl.
CPC ........ *A61B 5/02416* (2013.01); *A61B 5/0006* (2013.01); *A61B 5/02055* (2013.01);
(Continued)

(58) Field of Classification Search
CPC . A61B 5/02416; A61B 5/7203; A61B 5/6893; G06T 7/0012; G06T 2207/10048; B60W 40/08; B60W 2040/0872
See application file for complete search history.

(56) References Cited

U.S. PATENT DOCUMENTS

| | | | |
|---|---|---|---|
| 2012/0302846 A1* | 11/2012 | Volmer | G06K 9/624 600/324 |
| 2014/0275832 A1* | 9/2014 | Muehlsteff | A61B 5/02416 600/301 |

(Continued)

OTHER PUBLICATIONS

Zhang "Photoplethysmography-Based Heart Rate Monitoring in Physical Activities via Joint Sparse Spectrum Reconstruction" IEEE Transactions on Biomedical Engineering vol. 62, No. 8, Aug. 2015 (Year: 2015).*

(Continued)

*Primary Examiner* — Nathan J Jenness
(74) *Attorney, Agent, or Firm* — Gennadiy Vinokur; Hironori Tsukamoto

(57) ABSTRACT

A remote photoplethysmography (RPPG) system includes an input interface to receive a sequence of measurements of intensities of different regions of a skin of a person indicative of vital signs of the person; a solver to solve an optimization problem to determine frequency coefficients of photoplethysmographic waveforms corresponding to the measured intensities at the different regions, wherein the solver determines the frequency coefficients to reduce a distance between intensities of the skin reconstructed from the frequency coefficients and the corresponding measured intensities of the skin while enforcing joint sparsity on the frequency coefficients; and an estimator to estimate the vital signs of the person from the determined frequency coefficients of photoplethysmographic waveforms.

20 Claims, 11 Drawing Sheets

(51) Int. Cl.
  *B60W 40/08* (2012.01)
  *G06T 7/00* (2017.01)
  *A61B 5/0205* (2006.01)
  *A61B 5/08* (2006.01)
  *A61B 5/0295* (2006.01)
  *G06T 7/10* (2017.01)

(52) U.S. Cl.
  CPC .......... *A61B 5/0816* (2013.01); *A61B 5/7203* (2013.01); *A61B 5/7278* (2013.01); *B60W 40/08* (2013.01); *G06T 7/0012* (2013.01); *A61B 5/0008* (2013.01); *A61B 5/0295* (2013.01); *A61B 5/6893* (2013.01); *A61B 5/7275* (2013.01); *A61B 5/7282* (2013.01); *B60W 2040/0872* (2013.01); *G06T 7/10* (2017.01); *G06T 2207/10048* (2013.01)

(56) References Cited

U.S. PATENT DOCUMENTS

2018/0028123 A1* 2/2018 Ahmed ................ A61B 5/7221
2018/0153422 A1* 6/2018 Watanabe .......... A61B 5/02433

OTHER PUBLICATIONS

Nowara et al. "SparsePPG: Towards Driver Monitoring Using Camera-Based Vital Signs Estimation in Near-Infrared" IEEE/CVF Conference on Computer Vision and Pattern Recognition Workshops 2018 pp. 1352-1362 (Year: 2018).*

Zhang et al. "Respiratory rate estimation from the photoplethysmogram via joints parse signal reconstruction and spectra fusion" Biomedical Signal Processing and Control 35 (2017) 1-7 (Year: 2017).*

* cited by examiner

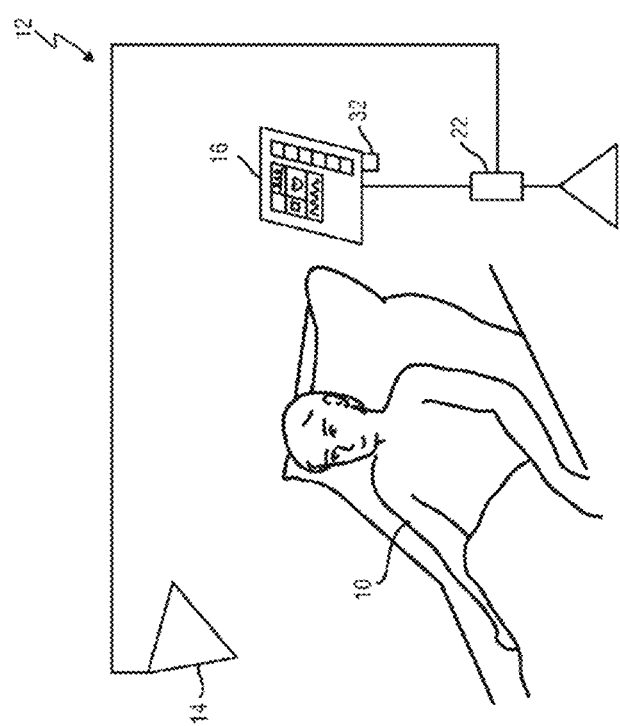

SYSTEM AND METHOD FOR REMOTE MEASUREMENTS OF VITAL SIGNS

TECHNICAL FIELD

This invention relates generally to remotely monitoring vital signs of a person and more particularly to remote photoplethysmographic (RPPG) measurements of the vital signs.

BACKGROUND

Vital signs of a person, for example the heart rate (HR), heart rate variability (HRV), the respiration rate (RR), or the blood oxygen saturation, serve as indicators of the current state of a person and as a potential predictor of serious medical events. For this reason, vital signs are extensively monitored in inpatient and outpatient care settings, at home, and in other health, leisure, and fitness settings. One way of measuring vital signs is plethysmography. Plethysmography generally refers to the measurement of volume changes of an organ or a body part and in particular to the detection of volume changes due to a cardiovascular pulse wave traveling through the body of a person with every heartbeat.

Photoplethysmography (PPG) is an optical measurement technique that evaluates a time-variant change of light reflectance or transmission of an area or volume of interest, which can be used to detect blood volume changes in the microvascular bed of tissue. PPG is based on the principle that blood absorbs and reflects light differently than surrounding tissue, so variations in blood volume with every heartbeat affect transmission or reflectance correspondingly. PPG is often used non-invasively to make measurements at the skin surface. The PPG waveform includes a pulsatile physiological waveform attributed to cardiac synchronous changes in the blood volume with each heartbeat, and is superimposed on a slowly varying baseline with various lower frequency components attributed to respiration, sympathetic nervous system activity, and thermoregulation. Although the origins of the components of the PPG signal are not fully understood, it is generally accepted that they can provide valuable information about the cardiovascular system.

Conventional pulse oximeters for measuring the heart rate and the (arterial) blood oxygen saturation of a person are attached to the skin of the person, for instance to a fingertip, earlobe or forehead. Therefore, they are referred to as 'contact' PPG devices. A typical pulse oximeter can include a combination of a green LED, a blue LED, a red LED, and an infrared LED as light sources and one photodiode for detecting light that has been transmitted through patient tissue. Commercially available pulse oximeters quickly switch between measurements at different wavelengths and thereby measure the transmissivity of the same area or volume of tissue at different wavelengths. This is referred to as time-division-multiplexing. The transmissivity over time at each wavelength gives the PPG waveforms for different wavelengths. Although contact PPG is regarded as a basically non-invasive technique, contact PPG measurement is often experienced as being unpleasant, since the pulse oximeter is directly attached to the person and any cables limit the freedom to move.

Recently, non-contact, remote PPG (RPPG) devices for unobtrusive measurements have been introduced. RPPG utilizes light sources or, in general, radiation sources disposed remotely from the person of interest. Similarly, a detector, e.g., a camera or a photo detector, can be disposed remotely from the person of interest. Therefore, remote photoplethysmographic systems and devices are considered unobtrusive and well suited for medical as well as non-medical everyday applications.

One of the advantages of camera-based vital signs monitoring versus on-body sensors is the high ease-of-use: there is no need to attach a sensor; just aiming the camera at the person is sufficient. Another advantage of camera-based vital signs monitoring over on-body sensors is the potential for achieving motion robustness: cameras have greater spatial resolution than contact sensors, which mostly include a single-element detector.

One of the challenges for RPPG technology is to be able to provide accurate measurements under motion/light distortions. Several methods have been developed to enable robust camera-based vital signs measurement. For such measurements, usually a plurality of signals is captured based on image processing of a captured image sequence. The plurality of signals may originate from different pixels of a sensor corresponding to different regions of a skin of a person and/or from different color channels of one pixel corresponding to the same spatial position. Then, photoplethysmographic waveforms are derived from the plurality of the signals. These photoplethysmographic waveforms are indicative of the vital signs of a person that can be determined by further analysis of the waveforms.

However, the quality of the photoplethysmographic waveforms is degraded to an extent determined by the value of the signal-to-noise ratio (SNR) of the sensed measurements. Low SNR due to light variations and false peaks in the photoplethysmographic waveforms due to motion have the potential to confound the PPG signal. To address these challenges, some methods perform an extensive analysis of a plurality of photoplethysmographic waveforms. For example, a method described in U.S. 2016/0220128 estimates a weighted combination of the plurality of the photoplethysmographic waveforms to reduce outliers caused by the noise. However, such an approach may not remove enough noise from the signal and may not always lead to an optimal result.

Accordingly, there is a need to reduce the sensitivity of the RPPG estimation to noise in the measurements of intensities (e.g., image pixel intensities) of a skin of a person.

SUMMARY

Some embodiments are based on recognition that the sensitivity of remote photoplethysmography (RPPG) to noise in the measurements of intensities (e.g., pixel intensities in camera images) of a skin of a person is caused at least in part by independent derivation of photoplethysmographic waveforms from the intensities of a skin of a person measured at different spatial positions. Some embodiments are based on recognition that at different positions, e.g., at different regions of the skin of the person, the measurement intensities can be subjected to different and sometimes even unrelated noise. To that end, the independent estimation of the photoplethysmographic waveforms from intensities of different regions of the skin of a person may fail to assist each other in identifying such noise.

Some embodiments are based on recognition that the effect of the noise on the quality of the RPPG estimation can be reduced by collectively estimating different photoplethysmographic waveforms of intensity of a skin of a person measured at different regions of the skin. Indeed, when RPPG is used to estimate a vital sign of a person, e.g., a heart rate, the heartbeat is a common source of intensity variations present in all regions of the skin. To that end, it can be beneficial to estimate the photoplethysmographic waveforms of different regions collectively, i.e., using a common metric.

Some embodiments are based on recognition that two types of noise are acting on the intensities of the skin, i.e., external noise and internal noise. The external noise effects the intensity of the skin due to external factors such as lighting variations, motion of the person, and resolution of the sensor measuring the intensities. The internal noise effects the intensity of the skin due to internal factors such as different effects of cardiovascular blood flow on the appearance of different regions of the skin of a person. For example, the heartbeat can affect the intensity of the forehead and cheeks of a person more than it affects the intensity of the nose.

Some embodiments are based on realization that both types of noise can be addressed in the frequency domain of the intensity measurements. Specifically, the external noise is often non-periodic or has a periodic frequency different than that of the signal of interest (e.g., the pulsatile signal), and thus can be detected in the frequency domain. In addition, the internal noise, while resulting in intensity magnitude variations or time-shifts of the intensity variations in different regions of the skin, preserves the periodicity of the common source of intensity variations in the frequency domain. To that end, some embodiments are based on realization that the common metric on the estimate the photoplethysmographic waveforms needs to be enforced in the frequency domain of the intensity measurements, rather than in the domain of the intensity measurements themselves.

Some embodiments are based on recognition that if the frequency coefficients of the photoplethysmographic waveforms are directly derived from the intensity measurements, the enforcement of the common metric in frequency domain on such a direct estimation can be problematic. However, it can be advantageous to enforce the common metric during the estimation of the frequency coefficients rather than after the frequency coefficients are estimated. To that end, some embodiments utilize an optimization framework to reconstruct the frequency coefficients of the photoplethysmographic waveforms to match the measured intensities, rather than to directly compute the frequency coefficients from the measured intensities. Such a reverse direction in the estimation of the frequency coefficients allows performing the reconstruction subject to constraints that can enforce the common metric on the frequency coefficients of different photoplethysmographic waveforms of different regions. Because such a reconstruction reverses a direction of the direct estimation of the frequency coefficients from the intensity measurements, such a reconstruction is referred herein as a reverse reconstruction.

Some embodiments are based on realization that, in the frequency domain, the common metric enforced on different photoplethysmographic waveforms can be joint sparsity of the frequency coefficients of the photoplethysmographic waveforms. The joint sparsity of the frequency coefficients forces different photoplethysmographic waveforms to be sparse together in the same frequency bins and/or to have large energy only in the same frequency bins. Such a joint sparsity adequately reflects the notion of the common source of intensity variations, and can jointly assist different photoplethysmographic waveforms to remove different and potentially unrelated outliers caused by the external and internal noise, making the RPPG less sensitive to noise.

To that end, some embodiments determine the frequency coefficients of photoplethysmographic waveforms of intensity signals of different regions of a person's skin in a way that minimizes the difference between the corresponding intensity signals estimated using the determined frequency coefficients and the measured intensity signals, while enforcing the joint sparsity on the determined frequency coefficients. For example, some embodiments estimate the intensity signals using an inverse Fourier transformation of the determined frequency coefficients. Such a reverse reconstruction allows reducing the sensitivity of the RPPG estimation to the measurement noise.

Some embodiments are based on recognition that the determination of the frequency coefficients can be represented as an optimization, e.g., a minimization, problem while the enforcement of the joint sparsity can be represented as a constraint on the optimization. In such a manner, the computational requirement for finding the frequency coefficients can be reduced. Some embodiments are based on recognition that the constraints can be enforced as a hard constraint prohibiting its violation or as a soft constraint penalizing its violation. Some embodiments enforce the hard constraint when the periodicity of the recovered vital sign is desired. Otherwise, an embodiment enforces the soft constraint. For example, one embodiment enforces the joint sparsity as a soft constraint for measuring the heart rate.

Some embodiments enforce the joint sparsity as a soft constraint by including in the optimization a weighted two-one norm of the frequency coefficients of different photoplethysmographic waveforms. The two-one norm component of the optimization promotes joint sparsity of frequency coefficients, while the weight of the two-one norm component determines the penalty for violation of this soft constraint. Thus, the weight of the two-one norm component can be used to vary a number of non-zero frequency coefficients, depending on the type of vital sign being measured.

Some embodiments acquire the intensity measurements as continuous signals over a significant time period, e.g., minutes, hours or even days. To reduce the computational requirements, some embodiments determine the vital signs sequentially for a sequence of temporal segments of those continuous signals. Those segments can be overlapping or adjoining to each other. However, some embodiments are based on recognition that the reverse reconstruction of the photoplethysmographic waveforms from the frequency coefficients can introduce discontinuities in the estimation of vital signs across different segments of the continuous signals.

To address this discontinuity problem, one embodiment uses the overlapping segments to determine the vital signs. At each control time step, the current segment includes a first portion corresponding to previously processed intensity measurements (from the previous segment, which was processed in the previous control time step) and a second portion corresponding to newly measured intensities. For the first portion of the segment, the embodiment uses the intensity signal reconstructed from the frequency coefficient determined for the first portion during the previous control step. The reconstructed intensity is then concatenated with the measured intensity of the second portion using a weighted average to form the intensity measurements of the current segment. Such a concatenation has an effect of smoothing the differences between processed and unprocessed signals, which reduces the discontinuity of the estimated vital signs.

It is an object of one embodiment to provide an RPPG system suitable for estimating vital signs of a person driving a vehicle. Such an RPPG system is useful for detecting changes in driver alertness and can help to prevent accidents. Unfortunately, the application of RPPG to driver monitoring presents several unique challenges. Specifically, during driving, illumination on the driver's face can change dramatically. For example, during the day, the sunlight is filtered by trees, clouds, and buildings before reaching the driver's face. As the vehicle moves, this direct illumination can change frequently and dramatically in both magnitude and spatial extent. At night, overhead streetlamps and headlights of approaching cars cause large intensity, spatially non-uniform changes in illumination. These illumination changes can be so dramatic and omnipresent that a number of approaches to mitigate these illumination variations are not practical.

To address these challenges, one embodiment uses active in-car illumination, in a narrow spectral band in which sunlight and streetlamp spectral energy are both minimal. For example, due to the water in the atmosphere, the sunlight that reaches the earth's surface has much less energy around the frequency of 940 nm than it does at other frequencies. The light output by streetlamps and vehicle headlights is typically in the visible spectrum, with very little power at infrared frequencies. To that end, one embodiment uses an active narrow-band illumination source at 940 nm and a camera filter at the same frequency, which ensures that much of the illumination changes due to environmental ambient illumination are filtered away. Further, since this narrow frequency band of 940 nm is beyond the visible range, humans do not perceive this light source and thus are not distracted by its presence. Moreover, the narrower the bandwidth of the light source used in the active illumination, the narrower the bandpass filter on the camera can be, which further rejects changes due to ambient illumination. For example, some implementations use an LED source and camera bandpass filters with 10 nm bandwidth.

Accordingly, one embodiment uses a narrow-bandwidth near-infrared (NIR) light source to illuminate the skin of the person at a narrow frequency band including a near-infrared frequency of 940 nm and a NIR camera to measure the intensities of different regions of the skin in the narrow frequency band. In such a manner, the measurements of the intensities of each of the different regions are single channel measurements.

Some embodiments are based on recognition that in the narrow frequency band including the near-infrared frequency of 940 nm, the signal observed by the NIR camera is significantly weaker than a signal observed by a color intensity camera, such as an RGB camera. However, the experiments demonstrated effectiveness of the sparse reconstruction RPPG used by some embodiments in handling the week intensity signals.

In addition, some embodiments are based on recognition that because the intensity signal measured by the NIR camera is weak, additional methods can be beneficial to increase the SNR of the measured intensities. To that end, one embodiment uses a filter to denoise the measurements of the intensities of each of the different regions using outlier-robust principal components analysis (RPCA). The RPCA used by this embodiment is computationally demanding and may not be necessary when the intensity signal has a high SNR, as in the case of using an RGB camera. However, for the measurements at 940 nm frequency band, those additional computations can be justified.

BRIEF DESCRIPTION OF THE DRAWINGS

FIG. 4A shows a schematic of RPPG system according to one example.

DETAILED DESCRIPTION

Figure 1A:
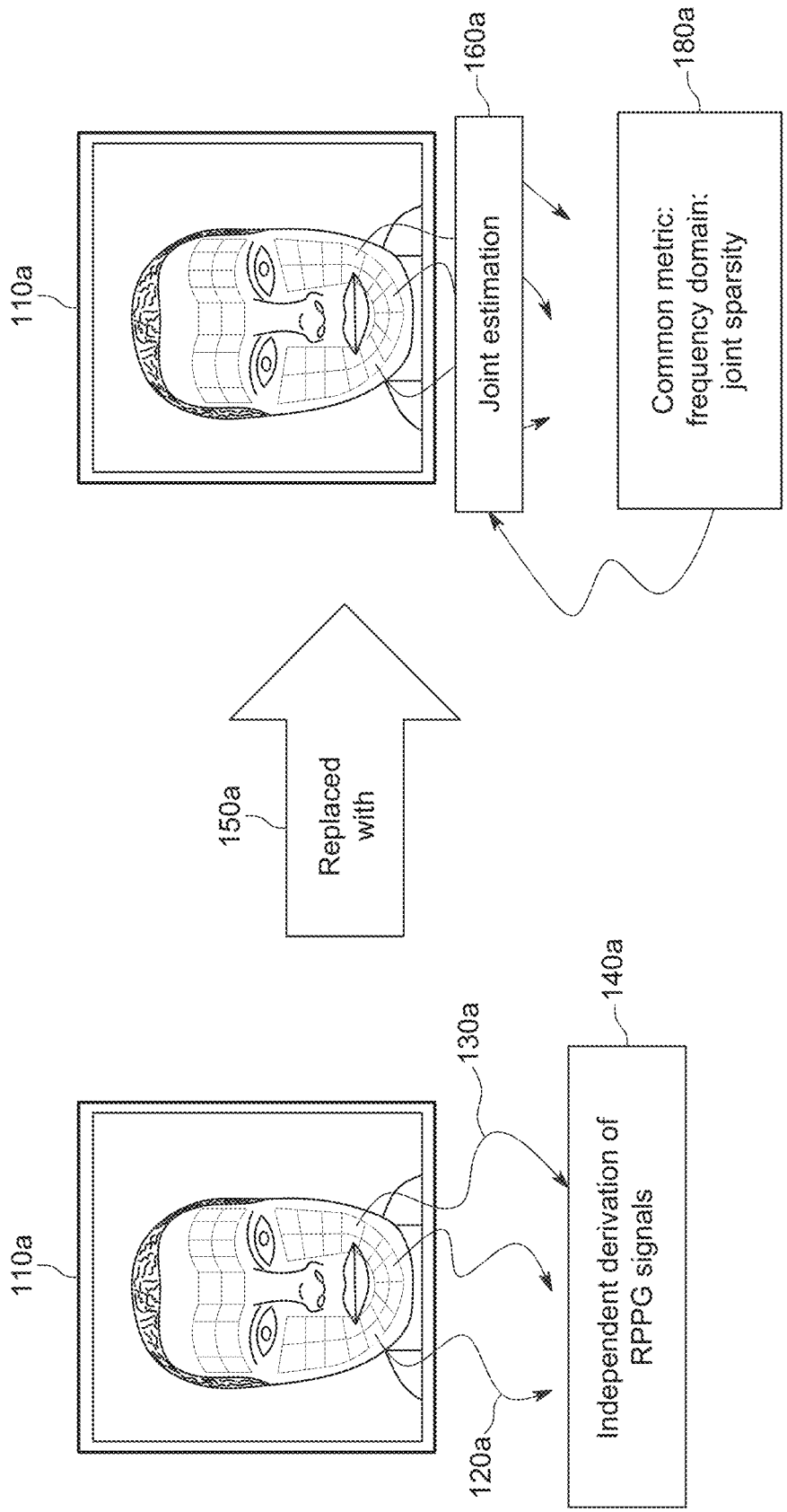
FIG. 1A shows a schematic illustrating some principles used by some embodiments to determine vital signs of the person using remote photoplethysmography (RPPG).

FIG. 1A shows a schematic illustrating some principles used by some embodiments to determine vital signs of the person using remote photoplethysmography (RPPG). Some embodiments are based on recognition that the sensitivity of the RPPG to noise in the measurements of intensities (e.g., pixel intensities in camera images) of a skin of a person $110a$ is caused at least in part by independent derivation $140a$ of photoplethysmographic waveforms from the intensities $120a$ and $130a$ of a skin of a person measured at different spatial positions. Some embodiments are based on recognition that at different positions, e.g., at different regions of the skin of the person, the measurement intensities can be subjected to different and sometimes even unrelated noise. To that end, photoplethysmographic waveforms that are independently estimated $140a$ of from intensities of different regions of the skin of a person may fail to assist each other in identifying such noise.

Some embodiments are based on recognition that measured intensities at different regions of the skin of the person can be subjected to different and sometimes even unrelated noise. In contrast, the heartbeat is a common source of intensity variations present in different regions of the skin. Thus, the effect of the noise on the quality of the RPPG estimation can be reduced when the independent estimation $140a$ is replaced $150a$ with a joint estimation $160a$ of different photoplethysmographic waveforms of intensity of a skin of a person measured at different regions of the skin. In this way, the embodiments can extract the PPG waveform that is common to many regions (including regions that may also contain considerable noise), while ignoring noise signals that are not shared across many regions.

Some embodiments are based on recognition that it can be beneficial to estimate the PPG waveforms of different regions collectively, i.e., using a common metric $180a$. Some embodiments are based on recognition that two types of noise are acting on the intensities of the skin, i.e., external noise and internal noise. The external noise affects the intensity of the skin due to external factors such as lighting variations, motion of the person, and resolution of the sensor measuring the intensities. The internal noise affects the intensity of the skin due to internal factors such as different effects of cardiovascular blood flow on the appearance of different regions of the skin of a person. For example, the heartbeat can affect the intensity of the forehead and cheeks of a person more than it affects the intensity of the nose.

Some embodiments are based on realization that both types of noise can be addressed in the frequency domain of the intensity measurements. Specifically, the external noise is often non-periodic or has a periodic frequency different than that of the signal of interest (e.g., the pulsatile signal), and thus can be detected in the frequency domain. In addition, the internal noise, while resulting in intensity magnitude variations or time-shifts of the intensity variations in different regions of the skin, preserves the periodicity of the common source of intensity variations in the frequency domain.

To that end, some embodiments are based on realization that the common metric used to estimate the photoplethysmographic waveforms of different regions should be enforced in the frequency domain $180a$ of the intensity measurements, rather than in the domain of the intensity measurements themselves. In addition, joint sparsity of the frequency coefficients forces different photoplethysmographic waveforms to be sparse together in the same frequency bins and/or to have large energy only in the same frequency bins. Hence, the joint sparsity adequately reflects the notion of the common source of intensity variations used by some embodiments.

Figure 1B:
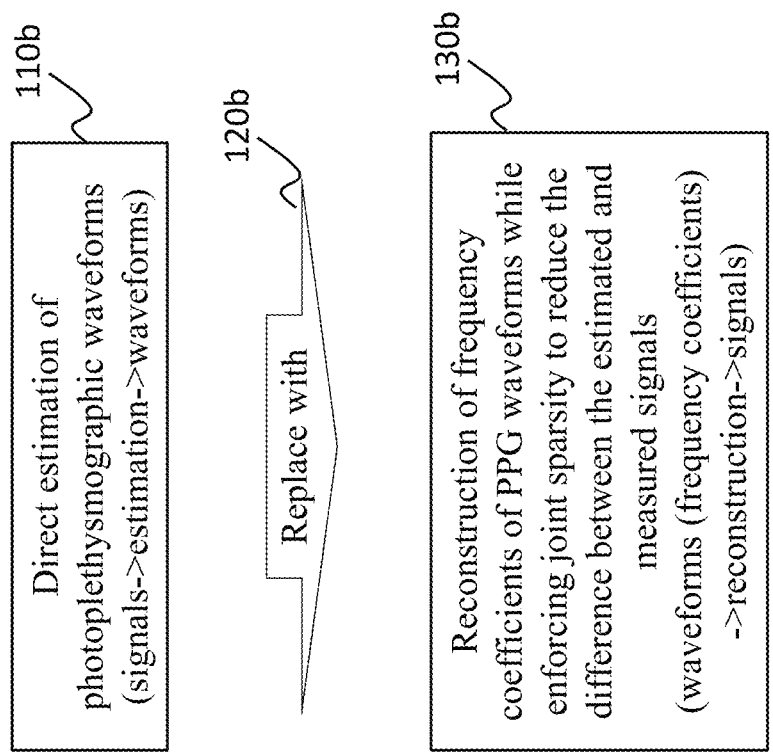
FIG. 1B shows a schematic of some principles used by some embodiments to enforce joint sparsity in frequency domain on joint estimation of photoplethysmography waveforms for different regions of the skin of a person.

FIG. 1B shows a schematic of some principles used by some embodiments to enforce joint sparsity in the frequency domain for joint estimation of photoplethysmographic waveforms for different regions of the skin of a person. Some embodiments are based on realization that since some vital signs, such as a heartbeat signal, are locally periodic and exist within all regions, this common metric should be enforced in the frequency domain. However, intensity measurements can be affected by noise that is also periodic. Therefore, if the frequency coefficients of photoplethysmographic waveforms are directly derived from the intensity measurements, the enforcement of the common metric in frequency domain on such a direct estimation is problematic.

However, some embodiments are based on another realization that direct estimation $110b$ of photoplethysmographic waveforms, i.e., the waveforms are derived from measurements, can be replaced $120b$ with an optimization framework to reconstruct $130b$ the frequency coefficients of the photoplethysmographic waveforms to match the measured intensities, rather than to directly compute the frequency coefficients from the measured intensities. Such a reverse direction in the estimation of the frequency coefficients allows performing the reconstruction subject to constraints that can enforce the common metric, i.e., the joint sparsity, on the frequency coefficients of different photoplethysmographic waveforms of different regions.

Figure 1C:
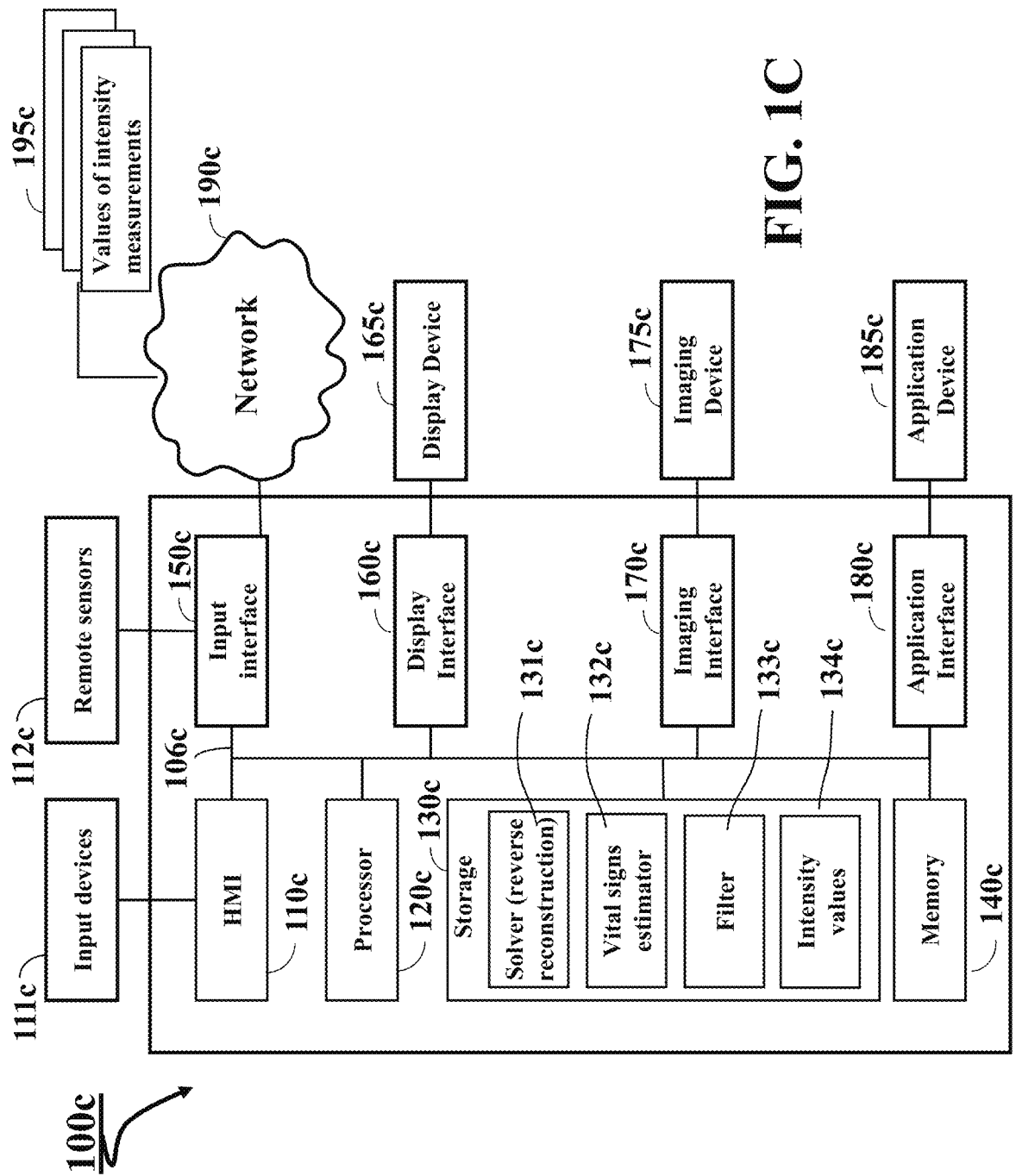
FIG. 1C shows a block diagram of a remote photoplethysmography (RPPG) system 100c in accordance with some embodiments.

FIG. 1C shows a block diagram of a remote photoplethysmography (RPPG) system $100c$ in accordance with some embodiments. The system $100c$ includes a processor $120c$ configured to execute stored instructions, as well as a memory $140c$ that stores instructions that are executable by the processor. The processor $120c$ can be a single core processor, a multi-core processor, a computing cluster, or any number of other configurations. The memory $140c$ can include random access memory (RAM), read only memory (ROM), flash memory, or any other suitable memory systems. The processor $120c$ is connected through a bus $106c$ to one or more input and output devices.

The instructions stored in the memory $140c$ implement an RPPG method for estimating the vital signs of the person from measurements of intensities of a skin of a person. To that end, the RPPG system $100c$ can also include a storage device $130c$ adapted to store intensity values $134c$ and various modules such as components $131c$, $132c$, and $133c$ executed by the processor $120c$ to perform the vital signs estimations. The storage device $130$ can be implemented using a hard drive, an optical drive, a thumb drive, an array of drives, or any combinations thereof.

For example, the RPPG system $100c$ includes a solver $131c$ to solve an optimization problem to determine frequency coefficients of photoplethysmographic waveforms corresponding to the measured intensities at the different regions. According to some principles employed by different embodiments, the solver determines the frequency coefficients to reduce a distance between intensities of the skin reconstructed from the frequency coefficients and the corresponding measured intensities of the skin while enforcing joint sparsity on the frequency coefficients. Such a reverse reconstruction of the frequency coefficients allows to enforce a common metric, i.e., the joint sparsity, in the frequency domain.

The RPPG system $100c$ includes an estimator $132c$ to estimate the vital signs of the person from the determined frequency coefficients of photoplethysmographic waveforms. In some implementations, the RPPG system $100c$ includes a filter $133c$ to denoise the measurements of the intensities of each of the different regions using robust principal components analysis (RPCA).

The system $100c$ includes an input interface $150c$ to receive a sequence of measurements of intensities of different regions of a skin of a person indicative of vital signs of the person. For example, the input interface can be a network interface controller adapted to connect the RPPG system $100c$ through the bus $106c$ to a network $190c$. Through the network $190c$, the values of intensity measurements $195c$ can be downloaded and stored as intensity values $134c$ within the computer's storage system $130c$ for storage and/or further processing.

Additionally, or alternatively, in some implementations, the RPPG system $100c$ is connected to a remote sensor $112c$, such as a camera, to collect the intensity values $134c$. In some implementations, a human machine interface (HMI) $110c$ within the system $100c$ connects the system to input devices $111c$, such as a keyboard, a mouse, trackball, touchpad, joy stick, pointing stick, stylus, or touchscreen, among others.

The RPPG system $100c$ can be linked through the bus $106c$ to an output interface to render the vital signs of the person. For example, the RPPG system $100c$ can include a display interface $160c$ adapted to connect the system $100c$ to a display device $165c$, wherein the display device $165c$ can include a computer monitor, camera, television, projector, or mobile device, among others.

The RPPG system $100c$ can also include and/or be connected to an imaging interface $170c$ adapted to connect the system to an imaging device $175c$. The imaging device $175c$ can include a video camera, computer, mobile device, webcam, or any combination thereof.

In some embodiments, the RPPG system $100c$ is connected to an application interface $180c$ through the bus $106c$ adapted to connect the RPPG system $100c$ to an application device $185c$ that can operate based on results of remote photoplethysmography. For example, in one embodiment, the device 185 is a car navigation system that uses the vital signs of a person to decide how to control, e.g., steer, the car. In other embodiments, the device may be used to control components of the vehicle. For instance, in one embodiment, the device 185 is a driver monitoring system, which uses the vital signs of the driver to determine when the driver is able to drive safely, e.g., whether the driver is drowsy or not.

Figure 1D:
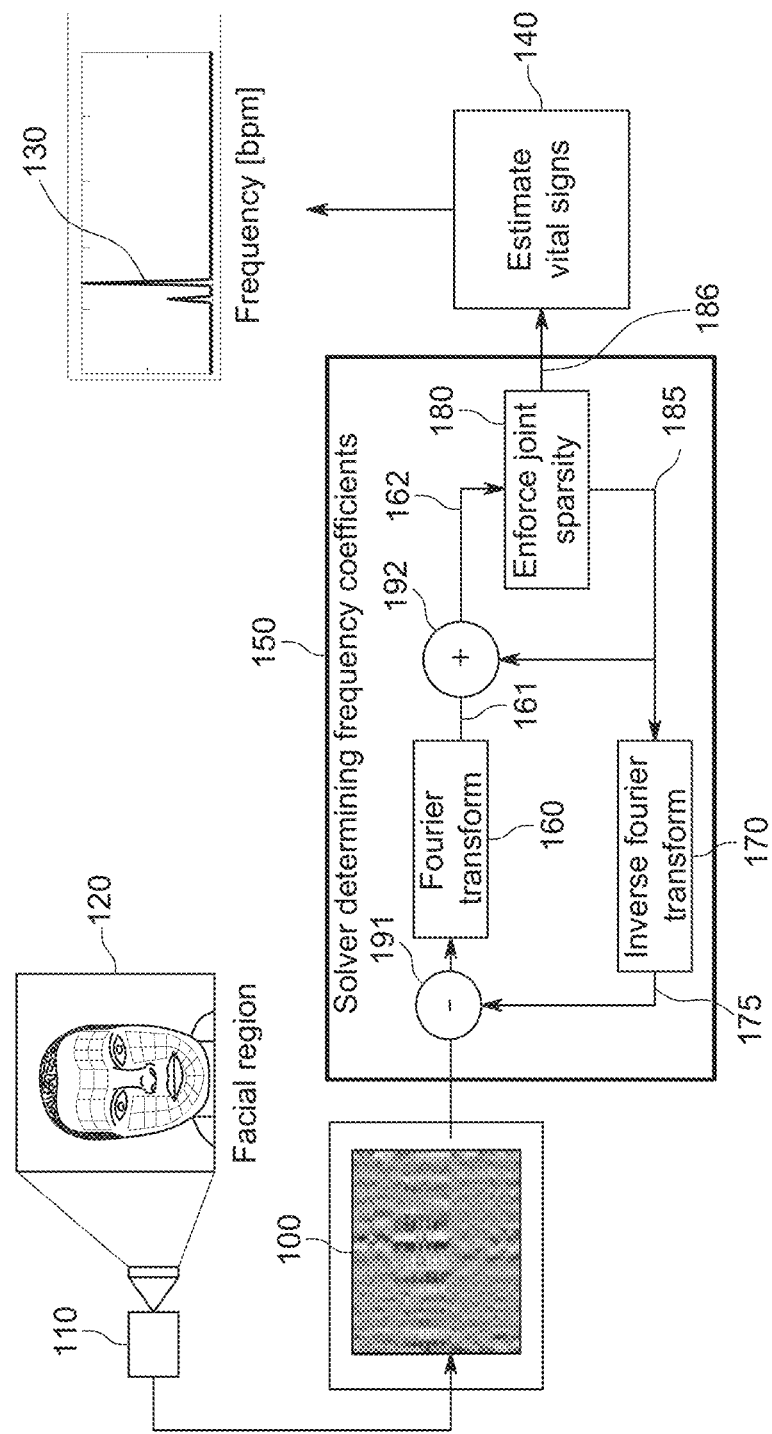
FIG. 1D shows a block diagram of an RPPG method according to one embodiment.

FIG. 1D shows a block diagram of RPPG method according to one embodiment. A set of different skin regions 120 of a person are measured using an input interface 110, such as a video camera that measures the intensity of the light reflecting off the skin as it varies over a period of time, to produce a raw RPPG matrix, P 100. The diagram shows skin regions that are located on the face (facial regions), but it is understood that various embodiments are not limited to using the face; other embodiments use other regions of exposed skin, such as the person's neck or wrists. The raw RPPG matrix 100, which includes measured intensities of the facial regions over time, is processed using a solver 150, which is an implementation of the solver 131c, that determines 140 frequency coefficients 130 that correspond to the person's vital signs through an iterative process.

In some implementations, the iterative process begins by setting estimated frequency coefficients 185 of all facial regions to 0 and computing an inverse Fourier transform 170 of the frequency coefficients 185 to produce estimated region intensities 175. These estimated region intensities 175, which represent the system's estimate of the RPPG signal, are then subtracted 191 from the raw RPPG matrix 100. The difference 191 between the raw RPPG matrix 100 and the estimated region intensities 175 is transformed using a Fourier transform 160 to produce temporary frequency coefficients 161. The temporary frequency coefficients 161 are added 192 to the estimated frequency coefficients 185 to produce updated frequency coefficients 162. The updated frequency coefficients 162 are modified to enforce joint sparsity 180, and the resulting frequency coefficients are used as the new estimated frequency coefficients 185. The new estimated frequency coefficients 185, which replace the previous iteration's estimated frequency coefficients 185, are used for a next iteration of the solver process 150.

In some embodiments, the solver enforces the joint sparsity as a soft constraint of the optimization problem, such that enforcing joint sparsity 180 forces the estimated frequency coefficients 185 to have nonzero values in only a small number of frequency bins, such that the nonzero bins are the same frequency bins across all facial regions. The iterative solver process 150 is repeated until a convergence condition 186 is met, for example, when the new estimated frequency coefficients 185 are essentially unchanged from the previous iteration's estimated frequency coefficients 185. After convergence 186, the estimated frequency coefficients 185 are output by the solver and are used to estimate vital signs 140. For example, in one embodiment an estimated vital sign is the frequency of the heartbeat 130 of the person over the period of time.

Figure 2:
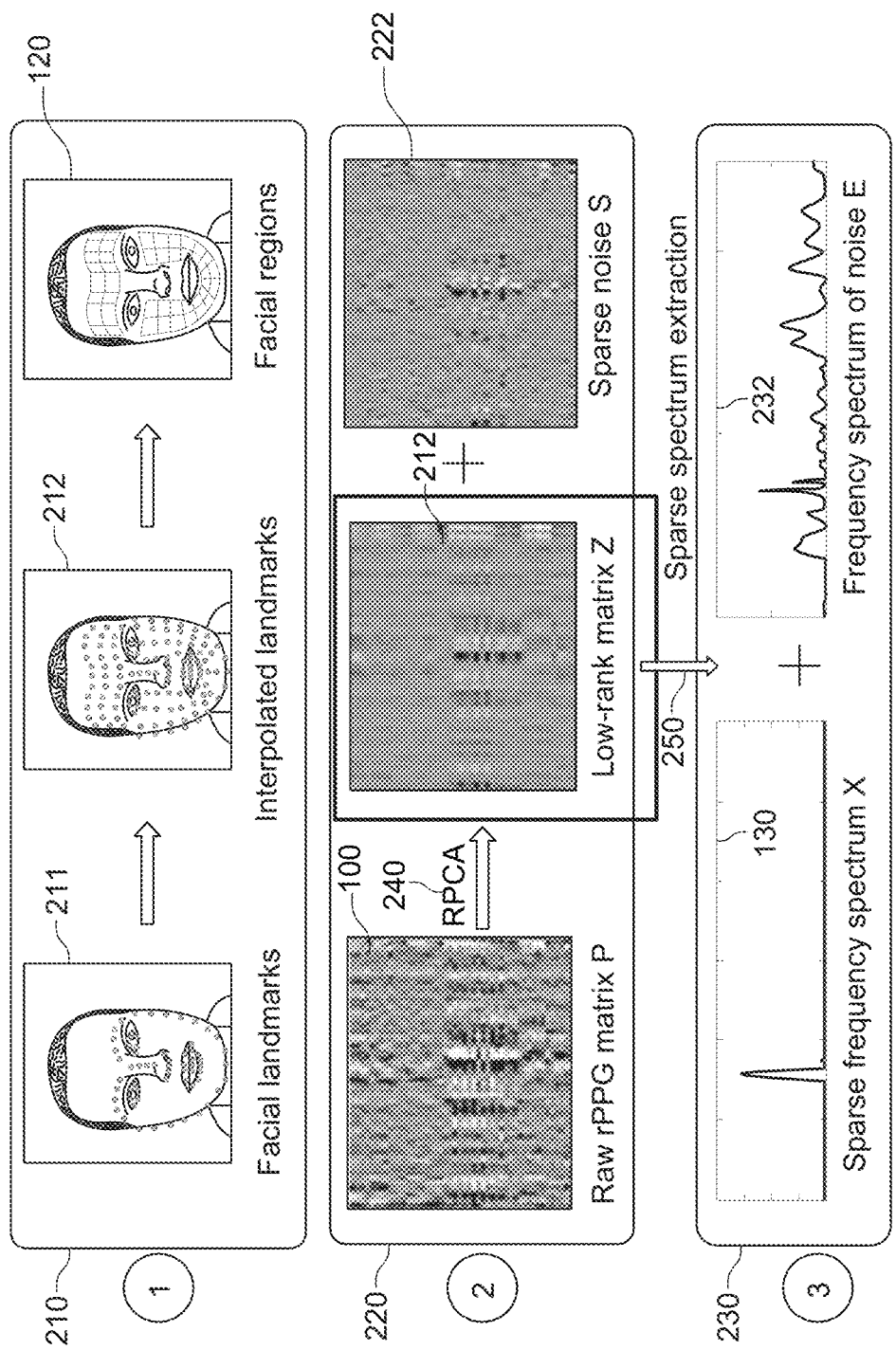
FIG. 2 shows a schematic of an exemplar RPPG method of some embodiments

FIG. 2 shows a schematic of an exemplar RPPG method of some embodiments adapted for RPPG signal tracking and denoising that can be applied to videos recorded with a combination of NIR illumination and unknown ambient lighting. In some implementations, the RPPG method extracts, tracks, and denoises the RPPG signal to obtain heart rate measurement. The method adaptively selects facial regions, i.e., a plurality of facial regions for which the desired vital sign contributes significantly to the raw RPPG signal, and denoises their estimated RPPG signals by relying on the fact that the pulsatile signal should be sparse in the frequency domain and low-rank across facial regions.

The RPPG method obtains 210 the raw RPPG signals from a video of a person by averaging the pixel intensity over all pixels in each of N skin regions 120 at each time step (e.g., each video frame). In some embodiments these skin regions 120 are facial regions that are focused around the forehead, cheeks, and chin area. In some embodiments, the RPPG method excludes areas along the face boundary as well as the eyes, nose, and mouth, since these areas exhibit weak RPPG signals.

For every facial region $j \in \{1, \ldots, N\}$, the measured intensity $p_j(t)$ is a one-dimensional time series signal, where $t \in \{1, \ldots, T\}$ is the temporal video frame index within a temporal window of length T. In some embodiments, the measured intensity $p_j(t)$ is the mean of the intensities of all pixels in region j at time t. In other embodiments, the measured intensity may be another measure of region intensity, such as the median intensity across the pixels in region j at time t, or some other robust average measure of the region's intensity.

In the general formulation, the RPPG method models the RPPG measurements from the N facial regions as a multi-channel signal acquisition scenario, in which every facial region j provides a different channel measurement of the underlying heartbeat signal contaminated by noise. In particular, one embodiment models the measured signals $p_j(t)$ as follows:

$$p_j(t) = h_j(t) * y_j(t) + n_j(t), \qquad (1)$$

where * is the linear convolution operator, $y_j(t)$ denotes the heartbeat signal observed at channel j, and $h_j(t)$ and $n_j(t)$ denote the channel response function and channel noise, respectively. Since the heartbeat signal is known to be sparse in the frequency domain, we rewrite (1) in vector form as shown below $$p_j = h_j * F^{-1} x_j + n_j, \qquad (2)$$

where F is the one-dimensional discrete Fourier transform of size T, and $x_j \in C^T$ denotes the sparse frequency spectrum of the heartbeat signal $y_j \in R^T$.

The signal model in (2) is a blind multichannel estimation problem that appears in fields such as wireless communications and sensor calibration. In particular, if $x_j = \bar{x}$ is fixed across all regions j, the problem is cast as the self-calibration from multiple snapshots model. The recoverability of these models relies on the ability to find low-dimensional characterizations of the channel responses $h_j$ and the sparse signal $\bar{x}$. These embodiments consider the following signal model:

$$p_j = F^{-1} x_j + n_j, \qquad (3)$$

where the sparse spectrum signals $x_j$ are not equal to each other, but they share the same support, i.e., the frequencies that have nonzero energy are mostly the same across all facial regions.

In some embodiments, the RPPG method denoises the measurements of the intensities of each of the different regions using robust principal components analysis (RPCA). For example, one embodiment processes the RPPG data by considering sliding time windows of length T. As shown in FIG. 2, for each time window, some embodiments stack the N RPPG signals into a T×N RPPG matrix P 100. In one embodiment, the columns of the matrix P are preprocessed by dividing the entries of each column by the average energy in the column. The process of dividing by the average intensity normalizes the range of intensities in the matrix P, allowing the processing to treat all regions equally.

The RPPG matrix 100 contains raw RPPG signals that can be contaminated by large amounts of noise due to factors such as inaccurate motion alignment, abrupt illumination changes, and variations in the strength of the RPPG signal across regions. However, all regions should express the same periodic physiological signal caused by the cardiac cycle (i.e., the pulsatile signal). Moreover, the periodicity of the underlying heartbeat signal over the duration of the temporal window induces a low-rank matrix when the noise is removed. Therefore, some embodiments model the RPPG matrix P 100 as the superposition of a low-rank matrix Y containing the heartbeat signal and a noise matrix N=E+S, where E denotes inlier noise 232 and S denotes outlier noise 222, such that $$P=Y+N=Y+E+S=Z+S. \quad (4)$$

For example, the outlier noise 222 arises from abrupt illumination changes and region tracking errors. These generally occur over a short time duration relative to the temporal processing window and affect a small number of regions. The inlier noise 232 characterizes regions of the face where the heartbeat signal is not the dominant driving harmonic. In this case, some embodiments suppress such regions from the heartbeat signal estimation. In order to extract an estimate of Y from P and suppress outliers, the embodiments follow a robust principal component analysis (RPCA) 240 approach and formulate the following optimization problem:

$$\min_{Z,S} \|Z\|_* + \gamma \|S\|_1 \text{ subject to } P = Z + S, \quad (5)$$

where $\|Z\|_* = \Sigma_k \sigma_k(Y)$ denotes the nuclear norm of the matrix Z, which equals the sum of its singular values $\sigma_k$. The $l_1$ norm of a matrix S is defined as $\|S\|_1 = \Sigma_{t,j} |S(t,j)|$, which equals the sum of the absolute values of its entries. The parameter γ controls the relative proportion of the signal energy that will be absorbed into the noise component S (e.g., in one embodiment we set γ=0.05). A smaller value of γ allows more of the signal to be considered as noise.

Various embodiments use different methods for solving optimization problem (5). For example, one embodiment splits the low-rank matrix Z into two factors $Z=LR^T$, where $L \in R^{T \times r}$, $R \in R^{N \times r}$, and r<T,N is a rank estimate parameter (e.g., in one embodiment we set rank r=12). Notice that the RPCA model is capable of eliminating sparse outlier noise 222 from the RPPG measurements making this approach fast and accurate.

An illustration of denoising the RPPG signals is RPCA 240 shown in section 220 of FIG. 2. However, it may happen in some instances that the signal from a facial region is noisy for the entire time window. Such a noise distribution could still be modeled as low-rank, and would therefore not be removed by RPCA. Some embodiments address such noise artifacts using sparse spectrum estimation 250.

For example, over a short time window, the heartbeat signal is approximately periodic, composed of a dominant frequency along with its harmonics. As a result, the frequency spectrum of a heartbeat signal should be sparse. Moreover, the same heartbeat signal drives the periodic behavior in the RPPG signals across all facial regions. Therefore, the noise-free frequency spectra $x_j$ of the signals $y_j$ from all regions j should have the same support.

Consider the signal model in (4), rewritten to model the denoised output of RPCA as $z_j = F^{-1}x_j + e_j$ and written in matrix form below:

$$Z = F^{-1}X + E = [F^{-1} \; I]\begin{bmatrix} X \\ E \end{bmatrix}, \quad (6)$$

where E 232 corresponds to the region level noise. Therefore, if a region is noisy, some embodiments absorb the entire time window (all samples) of that region into the matrix E. This can be achieved by forcing complete columns of E to be either zero or nonzero. On the other hand, since the frequency components in X 130 should be sparse and have the same support across all the regions, the columns of X are jointly sparse, i.e., the entire rows of X are either completely zero or nonzero.

Consequently, some embodiments define the following optimization problem to compute X 130 and E 232 from Z 221:

$$\min_{X,E} \frac{1}{2}\left\|Z - A\begin{bmatrix} X \\ E \end{bmatrix}\right\|_2^2 + \lambda\|X\|_{2,1} + \mu\|E^\top\|_{2,1}, \quad (7)$$

where we defined matrix A as the block matrix $A=[F^{-1} \; I]$, and the $l_{2,1}$ norm of a matrix X is defined as $$\|X\|_{2,1} = \Sigma_t \sqrt{\Sigma_j X(t,j)^2}. \quad (8)$$

In one embodiment, we set λ=0.2, μ=1. The solution to the above problem can be obtained using iterative shrinkage/thresholding methods, such as FISTA, where the shrinkage function should be applied appropriately to the row norms of X and column norms of E to produce the frequency spectra 230 of recovered signal X 130 and noise E 232.

In such a manner, the optimization problem includes a two-one norm of the frequency coefficients and a difference between the measured intensities and the intensities reconstructed from the frequency coefficients, wherein the two-one norm of the frequency coefficients is weighted or non-weighted. Enforcing the joint sparsity of X using an $l_{2,1}$ norm regularization forces facial regions to have nonzero frequency coefficients in at most a small number of frequency bins that are common to a plurality of facial regions, and sets all remaining frequency coefficients to zero.

Fusion of Time Windows

Since heartbeat signals vary slowly over time, we may consider the RPPG observations as multichannel measurements from a nearly stationary process. Therefore, we process the RPPG signals using a sliding window $$P = \begin{bmatrix} P_o \\ P_n \end{bmatrix}, \quad (9)$$

where $P_n$ denotes the new RPPG data that did not exist in the previous window, and $P_o$ is the portion of the previous (old) window's RPPG data that is also in the current window. For better noise suppression, we construct a weighted-average time-fused window $$\overline{P} = \alpha P + (1-\alpha)\begin{bmatrix} \tilde{Y}_o \\ P_n \end{bmatrix}, \quad (10)$$

where $\tilde{Y}=F^{-1}X$ is the filtered output of the previous time window, and $\tilde{Y}_o$ is the portion of $\tilde{Y}$ that is also present in the current window. The time-fused window $\bar{P}$ is then further denoised using the RPCA procedure, and the new sparse spectrum is estimated as described above.

In such a manner, the vital signs are determined iteratively for time windows defining different segments of the sequence of measurements. A segment of measurements for a current iteration includes a first portion and a second portion, the first portion is formed by intensities reconstructed from the frequency coefficients determined during the previous iteration for a time period corresponding to the first portion of the segment of the current iteration, and the second portion is formed by intensities measured for a time period of the second portion of the segment. In such a manner, discontinuity of vital signs estimation can be reduced.

For example, one embodiment uses a time window of duration 10 seconds and an overlap between time windows, where only 10 frames (0.33 seconds for videos recorded at 30 frames per second (fps)) come from the new time window, and we set the weight for averaging of time-fused windows to $\alpha=0.03$.

Preprocessing to Reject Facial Regions

Some facial regions are physiologically known to contain better RPPG signals. However, the "goodness" of these facial regions also depends on the particular video conditions, facial hair, or facial occlusions. Therefore, it is beneficial to identify which regions are likely to contain the most noise and remove them before any processing, so that they don't affect the signal estimates.

Figure 3:
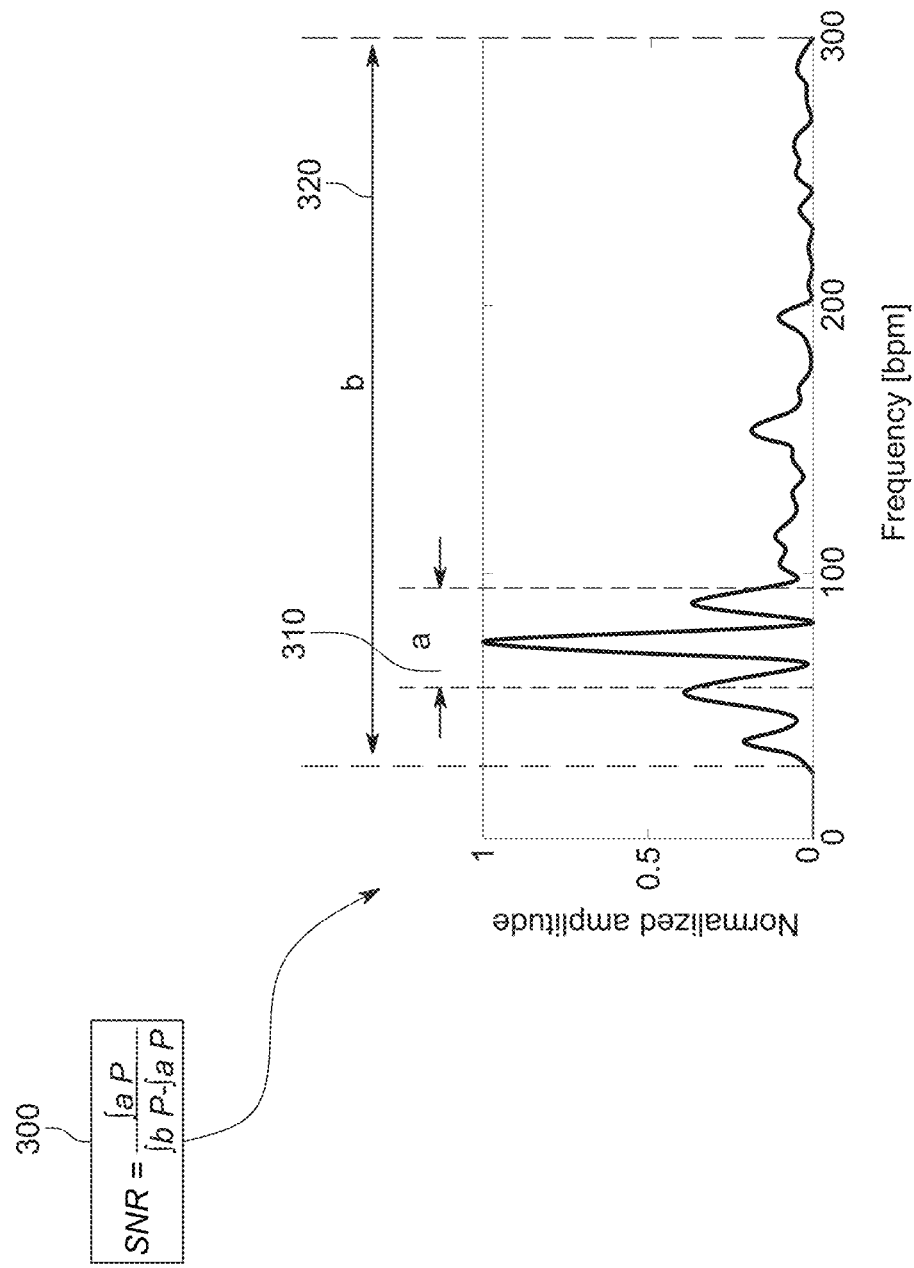
FIG. 3 shows a schematic of a power spectrum curve used for determining signal-to-noise ratio (SNR) of the RPPG signal used by some embodiments to evaluate usefulness of different regions.

FIG. 3 shows a schematic of a power spectrum curve used for determining signal-to-noise ratio (SNR) of the RPPG signal used by some embodiments to evaluate usefulness of different regions. For example, some embodiments do so by throwing away a region if its SNR is below a threshold $\theta_{SNR}$ (e.g., $\theta_{SNR}=0.2$) or if its maximum amplitude is above a threshold $\theta_{amp}$. For example, one embodiment sets $\theta_{amp}$ to be four times the average RPPG signal amplitude and/or the SNR is determined 300 as the ratio of the area under the power spectrum curve in a region 310 surrounding the maximum peak in the frequency spectrum, divided by the area under the curve in the rest of the frequency spectrum in a frequency range that contains the physiological range 320 of heartbeat signals (e.g., from 30 to 300 beats per minute (bpm)).

Some embodiments, within each time window, can reject different facial regions. To perform fusion of time windows, the embodiments first recompose the signal X in the missing regions by interpolating from neighboring regions.

EXEMPLAR IMPLEMENTATION(S)

To compute the raw RPPG signals P 100, some embodiments first use a face alignment (i.e., facial landmark detection) method to detect a number (e.g., 68) of facial landmarks 211, then interpolate and extrapolate the detected landmarks to a larger number (e.g., 145) of interpolated landmarks 212 to include the forehead region and subdivide the face into more regions. We use the facial landmarks to divide the face into a number (e.g., 48) of facial regions 120.

Since pixel intensity changes due to the heartbeat are a small fraction of each pixel's intensity, it is necessary to average pixels' intensities over a region of the face in order to get a consistent signal. However, this signal is still sensitive to which pixels are included in the region. In some embodiments, we re-detect the facial regions in each video frame. However, applying a face alignment algorithm independently to each frame can cause regions to move a small amount from one frame to the next, and this change in which pixels are included in a region can add extra noise that makes it difficult to estimate the vital sign of interest. To minimize such noise, some embodiments track the facial landmarks or the facial regions of interest. For example, one embodiment tracks the facial regions using a Kanade-Lucas-Tomasi (KLT) tracker and the RANSAC method. In each frame, the embodiment spatially averages the pixel intensities in each facial region to obtain a raw RPPG signal. The embodiment subtracts the mean intensity over time of each region's signals and use a bandpass filter to restrict the signals to the frequency range [30 bpm, 300 bpm], which includes the physiological range of the cardiac signals of interest.

To combine the denoised signals from each facial region, we take a median in each frequency bin across the regions of X. We use the median because it obtains an average that is robust to outliers, but other embodiments can use other averaging methods, such as a mean, in place of the median. The estimate of the heart rate in the time window is the frequency component for which the power of the frequency spectrum is maximum.

FIG. 4A shows a schematic of RPPG system according to one example. In this example, a patient 10 being hospitalized in a hospital bed. In such a hospitalization scenario the vital signs of the patient 10 need to be monitored. Conventional monitoring systems thereby usually rely on attachable sensors, i.e. body mounted sensors. In order to increase patient comfort, remote monitoring systems can be used, which can reduce the required cabling. In FIG. 4A there is illustrated a monitoring system 12 for remotely monitoring a vital sign of a patient 10 according to an aspect of the present invention. The illustrated system 12 thereby makes use of the remote photoplethysmographic measurement principle. Thereby, a camera 14 is used to capture an image, i.e., a video sequence of the patient 10.

This camera can include a CCD or CMOS sensor for converting incident light and the intensity variations thereof into an electronic signal. The camera 14 particularly non-invasively captures light reflected from a skin portion of the patient 10. A skin portion may thereby particularly refer to the forehead or the chest of the patient. A light source, e.g. an infrared or visible light source, may be used to illuminate the patient or a region of interest including a skin portion of the patient. It may also be possible that the patient 10 is illuminated with light of a certain limited spectrum or that two specific spectra (i.e. colors) are captured separately in order to analyze differences resulting therefrom. Based on the captured images, information on a vital sign of the patient 10 can be determined. In particular, vital signs such as the heart rate, the breathing rate or the blood oxygenation of the patient 10 can be determined. The determined information is usually displayed on an operator interface 16 for presenting the determined vital sign. Such an operator interface 16 may be a patient bedside monitor or may also be a remote monitoring station in a dedicated room in a hospital or even in a remote location in telemedicine applications. Prior to being able to display vital sign information, the detected images need to be processed. The detected images may, however, comprise noise components. The main sources of noise are motion of the patient 10 and (ambient) light fluctuations. Hence, an appropriate signal processing is required. Usually, a plurality of time signals being more or less representative of vital signs (heart rate, breathing rate, blood oxygen saturation) is acquired. The acquisition may thereby be operated on a specific spectral range (visible, infrared, combination of selected spectral bands), maybe operated at global or local level (one time signal per skin measurement area versus several signals originating from the skin measurement area) and may involve techniques like principal component analysis, independent component analysis, local density approximation, linear projection into color subspaces, or signal decomposition techniques like wavelets, sinusoidal modeling, and Empirical Mode Decomposition (EMD).

Figure 4B:
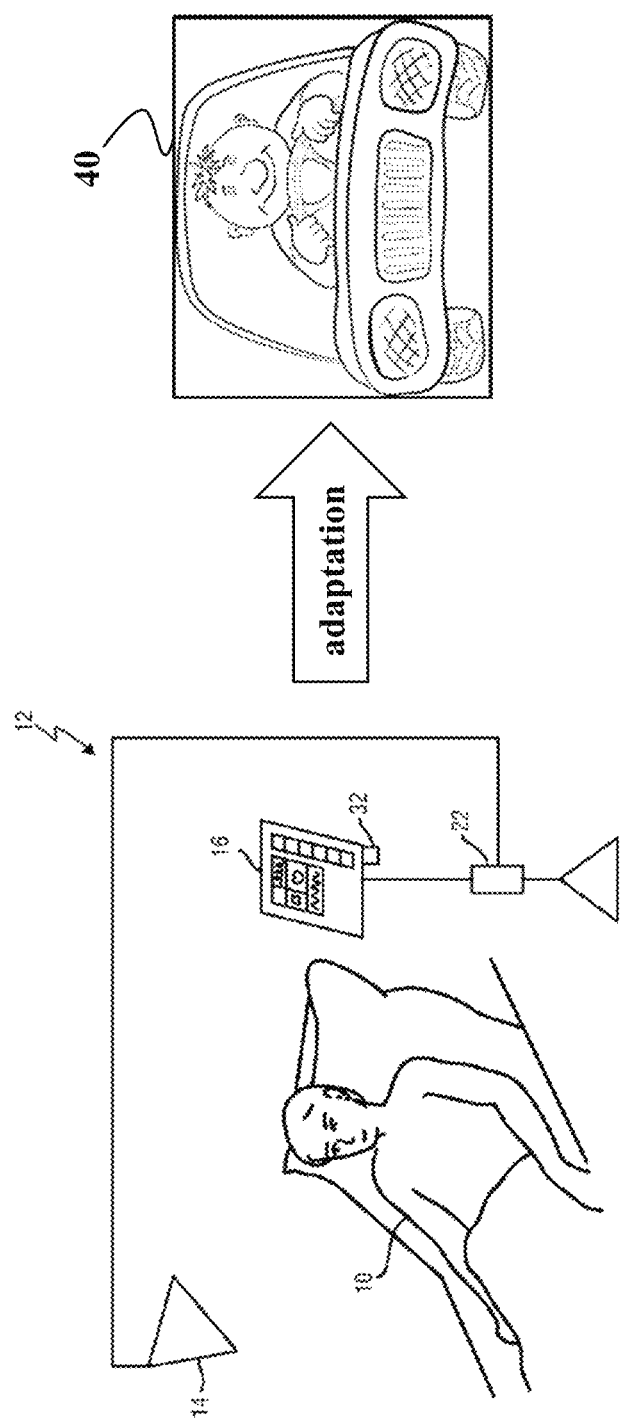
FIG. 4B shows a schematic of RPPG system according to another example.

FIG. 4B shows a schematic of RPPG system according to another example. In this example, the system 12 is adapted from a control environment of a hospital room to a volatile environment of the Driver Monitoring System (DMS) 40 to provide accurate measurements under motion/light distortions.

To that end, some embodiments provide an RPPG system suitable for estimating vital signs of a person driving a vehicle. Such an RPPG system is useful for detecting changes in driver alertness and can help to prevent accidents. Unfortunately, the application of RPPG to driver monitoring presents several unique challenges. Specifically, during driving, illumination on the driver's face can change dramatically. For example, during the day, the sunlight is filtered by trees, clouds, and buildings before reaching the driver's face. As the vehicle moves, this direct illumination can change frequently and dramatically in both magnitude and spatial extent. At night, overhead streetlamps and headlights of approaching cars cause large intensity, spatially non-uniform changes in illumination. These illumination changes can be so dramatic and omnipresent that a number of approaches to mitigate these illumination variations are not practical.

To address these challenges, additionally or alternatively to sparse reconstruction with joint sparsity disclosed above, one embodiment uses active in-car illumination, in a narrow spectral band in which sunlight and streetlamp spectral energy are both minimal.

Figure 5:
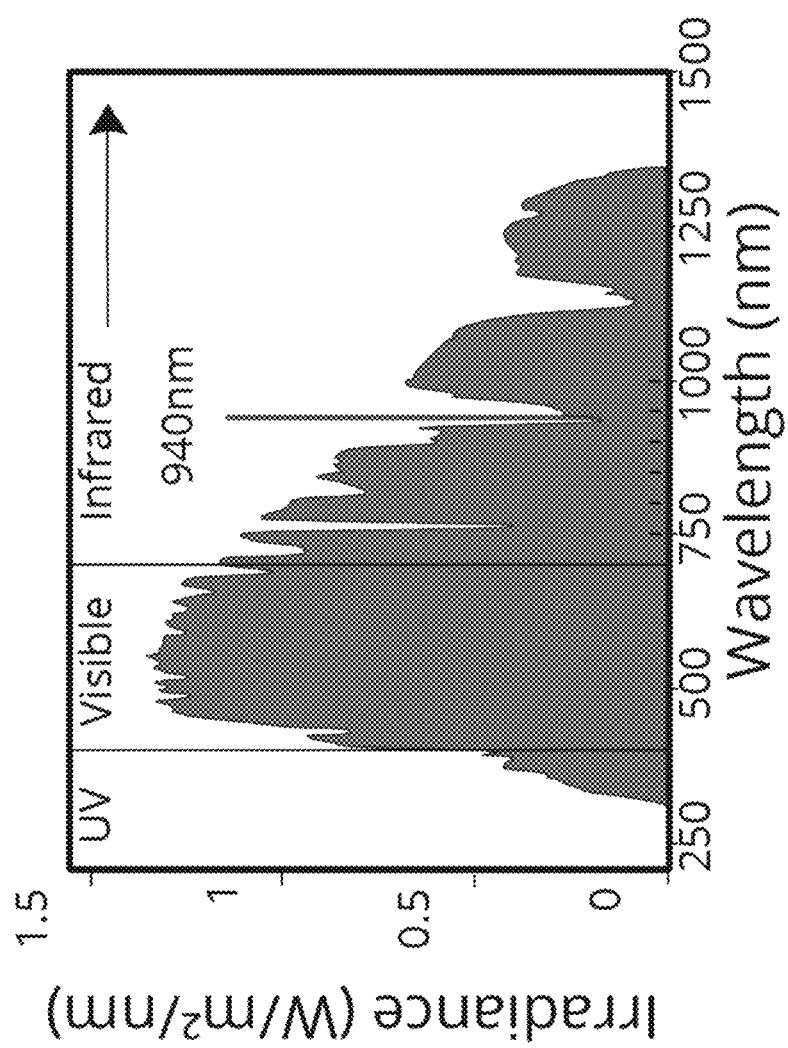
FIG. 5 shows a plot of a spectrum of sunlight at the Earth's surface used by some embodiments.

FIG. 5 shows a plot of a spectrum of sunlight at the Earth's surface used by some embodiments. For example, due to the water in the atmosphere, the sunlight that reaches the earth's surface has much less energy around the frequency of 940 nm than it does at other frequencies. The light output by streetlamps and vehicle headlights is typically in the visible spectrum, with very little power at infrared frequencies. To that end, one embodiment uses an active narrow-band illumination source at 940 nm and a camera filter at the same frequency, which ensures that much of the illumination changes due to environmental ambient illumination are filtered away. Further, since this narrow frequency band of 940 nm is beyond the visible range, humans do not perceive this light source and thus are not distracted by its presence. Moreover, the narrower the bandwidth of the light source used in the active illumination, the narrower the bandpass filter on the camera can be, which further rejects changes due to ambient illumination. For example, some implementations use an LED source and camera bandpass filters with 10 nm bandwidth.

Accordingly, one embodiment uses a narrow-bandwidth near-infrared (NIR) light source to illuminate the skin of the person at a narrow frequency band including a near-infrared frequency of 940 nm and a NIR camera to measure the intensities of different regions of the skin in the narrow frequency band. In such a manner, the measurements of the intensities of each of the different regions are single channel measurements.

Some embodiments are based on recognition that in the narrow frequency band including the near-infrared frequency of 940 nm, the signal observed by the NIR camera is significantly weaker than a signal observed by a color intensity camera, such as an RGB camera. However, the experiments demonstrated effectiveness of the sparse reconstruction RPPG used by some embodiments in handling the week intensity signals.

Figure 6:
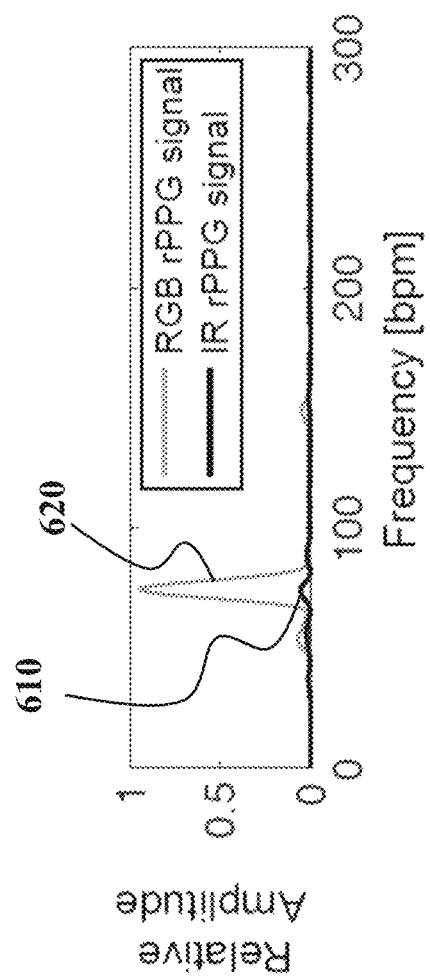
FIG. 6 shows a plot for comparison of RPPG signal frequency spectrum in IR and RGB.

FIG. 6 shows a plot for comparison of RPPG signal frequency spectrum in IR and RGB. The RPPG signal in IR 610 is about 10 times weaker than in RGB 620. Therefore, the RPPG system of one embodiment includes a near-infrared (NIR) light source to illuminate the skin of the person, wherein the NIR light source provides illumination in a first frequency band, and a camera to measure the intensities of each of the different regions in a second frequency band overlapping the first frequency band, such that the measured intensities of a region of the skin are computed from intensities of pixels of an image of the region of the skin.

The first frequency band and the second frequency band include a near-infrared frequency of 940 nm. The system includes a filter to denoise the measurements of the intensities of each of the different regions using robust principal components analysis (RPCA). The second frequency band, which in one embodiment is determined by a bandpass filter on the camera, has a passband of width less than 20 nm, e.g., the bandpass filter has a narrow passband whose full width at half maximum (FWHM) is less than 20 nm. In other words, the overlap between the first frequency band and the second frequency band is less than 20 nm wide. Such a system in combination with sparse reconstruction is able to perform RPPG for DMS environment.

Some embodiments incorporate the realization that optical filters such as bandpass filters and long-pass filters (i.e., filters that block transmission of light whose wavelength is less than a cutoff frequency but allow transmission of light whose wavelength is greater than a second, often equal, cutoff frequency) may be highly sensitive to the angle of incidence of the light passing through the filter. For example, an optical filter may be designed to transmit and block specified frequency ranges when the light enters the optical filter parallel to the axis of symmetry of the optical filter (roughly perpendicular to the optical filter's surface), which we will call an angle of incidence of 0°. When an angle of incidence varies from 0°, many optical filters exhibit "blue shift," in which the passband and/or cutoff frequencies of the filter effectively shift to shorter wavelengths. To account for this blue shift phenomenon, some embodiments use a center frequency of the overlap between the first and second frequency bands to have a wavelength greater than 940 nm (e.g., they shift the center frequency of a bandpass optical filter or the cutoff frequencies of a long-pass optical filter to have a longer wavelength than 940 nm).

Furthermore, because light from different parts of the skin will be incident upon the optical filter at different angles of incidence, the optical filter allows different transmission of light from different parts of the skin. To compensate for this, some embodiments use a bandpass filter with a wider passband, e.g., the bandpass optical filter has a passband that is wider than 20 nm, and hence the overlap between the first and second frequency bands is greater than 20 nm wide.

Figure 7:
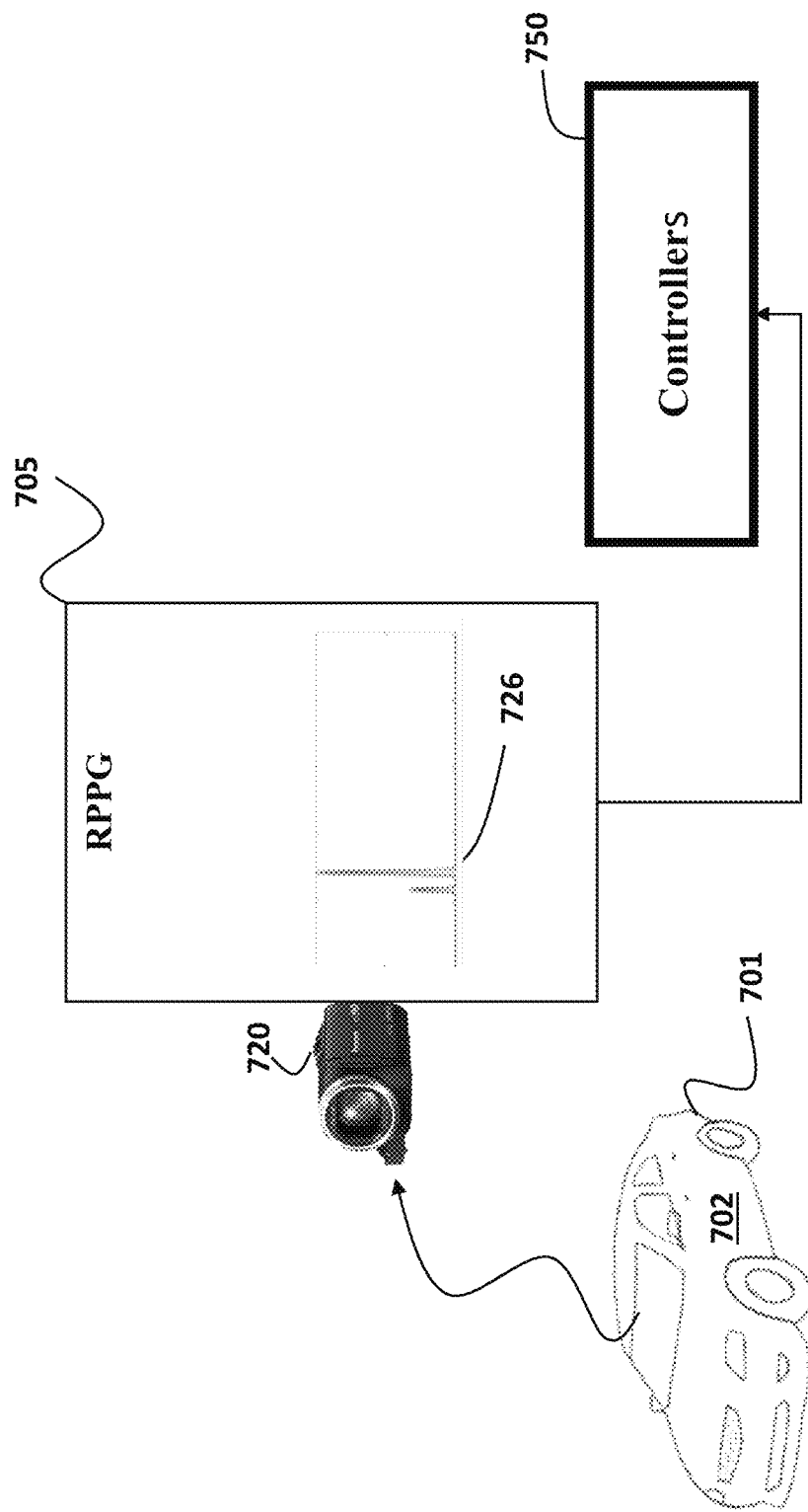
FIG. 7 shows a schematic of a vehicle including a processor for running an RPPG method to produce vital signs of a person in the vehicle according to one embodiment.

FIG. 7 shows a schematic of a vehicle 701 including a processor 702 for running a RPPG 705 to produce vital signs 726 of a person in the vehicle according to one embodiment. In this embodiment, the NIR light source and/or the NIR camera 720 are arranged in the vehicle 701. For example, the NIR light source is arranged in the vehicle to illuminate the skin of the person driving the vehicle, and the NIR camera 720 is arranged in the vehicle to measure the intensities of different regions of the skin of the person driving the vehicle. This embodiment also includes a controller 750 to execute a control action based on the estimated vital signs of the person driving the vehicle. For example, the controller can reduce a speed of the vehicle and/or change a steering of the vehicle.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. A processor may be implemented using circuitry in any suitable format.

Also, the embodiments of the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Although the invention has been described by way of examples of preferred embodiments, it is to be understood that various other adaptations and modifications can be made within the spirit and scope of the invention.

Therefore, it is the object of the appended claims to cover all such variations and modifications as come within the true spirit and scope of the invention.

The invention claimed is:

1. A remote photoplethysmography (RPPG) system, comprising: a processor; and memory having instructions stored thereon that, when executed by the processor, cause the RPPG system to:
   transform intensities of pixels of one or multiple images of a skin of a person into a sequence of measurements of intensities of different regions of the skin of the person indicative of vital signs of the person;
   solve an optimization problem to determine frequency coefficients of photoplethysmographic waveforms corresponding to the measured intensities at each of the different regions to reduce a difference between intensities of the skin of different regions reconstructed from the frequency coefficients of corresponding regions and the corresponding measured intensities of the skin while enforcing joint sparsity on the frequency coefficients of different regions, wherein the joint sparsity is enforced on the optimization problem as a constraint specifying that the frequency coefficients of each region have more zero elements than non-zero elements and the non-zero elements of the frequency coefficients of different regions belong to the same frequency bins;
   estimate the vital signs of the person from the frequency coefficients of photoplethysmographic waveforms determined for different regions;
   output the estimated vital signs of the person; and
   submit the estimated vital signs to a controller of a vehicle configured to execute a control action based on the estimated vital signs of the person driving the vehicle.

2. The RPPG system of claim 1, wherein the constraint enforces the joint sparsity as a soft constraint of the optimization problem.

3. The RPPG system of claim 1, wherein the optimization problem includes a two-one norm of the frequency coefficients and the difference between the measured intensities and the intensities reconstructed from the frequency coefficients, wherein the two-one norm of the frequency coefficients is weighted or non-weighted.

4. The RPPG system of claim 1, wherein the vital signs are determined iteratively for different segments of the sequence of measurements, wherein a segment of measurements for a current iteration includes a first portion and a second portion, the first portion is formed by intensities reconstructed from the frequency coefficients determined during the previous iteration for a time period corresponding to the first portion of the segment of the current iteration, and the second portion is formed by intensities measured for a time period of the second portion of the segment.

5. A device communicatively connected to the RPPG system of claim 1, comprising:
   a camera configured to measure the intensities of pixels of the images of the skin of the person; and
   a display device configured to render the vital signs of the person.

6. The device of claim 5, wherein the camera includes an optical filter configured to produce the intensities of the pixels of the image of different regions of the skin of the person in a non-visible frequency band including a near-infrared frequency corresponding to a wavelength of 940 nm.

7. The RPPG system of claim 1, further comprising:
   a near-infrared (NIR) light source to illuminate the skin of the person, wherein the NIR light source provides illumination in a first frequency band, and
   a camera to measure the intensities of each of the different regions in a second frequency band overlapping the first frequency band, such that the measured intensities of a region of the skin are computed from intensities of pixels of an image of the region of the skin.

8. The RPPG system of claim 7, wherein the first frequency band and the second frequency band include a near-infrared wavelength of 940 nm, wherein the overlap between the first frequency band and the second frequency band is less than or equal to 20 nm wide, further comprising:
   a filter to denoise the measurements of the intensities of each of the different regions using robust principal components analysis (RPCA).

9. The RPPG system of claim 7, wherein the overlap between the first frequency band and the second frequency band is centered at a wavelength greater than 940 nm, wherein the overlap between the first frequency band and the second frequency band is greater than 20 nm wide, further comprising:
   a filter to denoise the measurements of the intensities of each of the different regions using robust principal components analysis (RPCA).

10. A control system for controlling at least one component of the vehicle, comprising:
the RPPG system of claim 7, wherein the NIR light source is arranged in the vehicle to illuminate the skin of the person driving the vehicle, and wherein the camera is arranged in the vehicle to measure the intensities of different regions of the skin of the person driving the vehicle; and
the controller to execute a control action based on the estimated vital signs of the person driving the vehicle.

11. The RPPG system of claim 1, wherein the sequence of measurements of intensities of a region of the skin is a mean or a median of intensities of pixels of an image of the region of the skin acquired by a camera.

12. The RPPG system of claim 11, wherein the intensities of pixels belong to a single channel of the image.

13. The RPPG system of claim 11, wherein the region of the skin is a region on a face of the person identified by the camera using automatic facial landmark localization.

14. The RPPG system of claim 1, wherein to estimate the vital signs at each instant of time, the processor is configured to combine corresponding elements of the frequency coefficients of different regions that belong to the same frequencies to produce median frequency coefficients and reconstruct the vital signs from the median frequency coefficients.

15. The RPPG system of claim 1, wherein the vital signs include a pulse rate of the person.

16. A remote photoplethysmography (RPPG) method, wherein the method uses a processor coupled with stored instructions implementing the method, wherein the instructions, when executed by the processor carry out steps of the method, comprising:
transforming intensities of pixels of one or multiple images of a skin of a person into a sequence of measurements of intensities of different regions of the skin of the person indicative of vital signs of the person;
solving an optimization problem to determine frequency coefficients of photoplethysmographic waveforms corresponding to the measured intensities at each of the different regions to reduce a difference between intensities of the skin of different regions reconstructed from the frequency coefficients of corresponding regions and the corresponding measured intensities of the skin while enforcing joint sparsity on the frequency coefficients of different regions, wherein the joint sparsity is enforced on the optimization problem as a constraint specifying that the frequency coefficients of each region have more zero elements than non-zero elements and the non-zero elements of the frequency coefficients of different regions belong to the same frequency bins;
estimating the vital signs of the person from the frequency coefficients of photoplethysmographic waveforms determined for different regions; and
submitting the estimated vital signs to a controller of a vehicle configured to execute a control action based on the estimated vital signs of the person driving the vehicle.

17. The RPPG method of claim 16, wherein the optimization problem includes a two-one norm of the frequency coefficients and a difference between the measured intensities and the intensities reconstructed from the frequency coefficients, wherein the two-one norm of the frequency coefficients is weighted or non-weighted, wherein the vital signs are determined iteratively for different segments of the sequence of measurements, wherein a segment of measurements for a current iteration includes a first portion and a second portion, the first portion is formed by intensities reconstructed from the frequency coefficients determined during the previous iteration for a period of the first portion of the segment and the second portion is formed by intensities measured for a period of the second portion of the segment.

18. The RPPG method of claim 16, wherein the intensities of different regions of the skin of the person are measured in a frequency band including a near-infrared frequency of 940 nm.

19. A non-transitory computer-readable storage medium embodied thereon a program executable by a processor for performing a method, the method comprising:
transforming intensities of pixels of one or multiple images of a skin of a person into a sequence of measurements of intensities of different regions of the skin of the person indicative of vital signs of the person;
solving an optimization problem to determine frequency coefficients of photoplethysmographic waveforms corresponding to the measured intensities at each of the different regions to reduce a difference between intensities of the skin of different regions reconstructed from the frequency coefficients of corresponding regions and the corresponding measured intensities of the skin while enforcing joint sparsity on the frequency coefficients of different regions, wherein the joint sparsity is enforced on the optimization problem as a constraint specifying that the frequency coefficients of each region have more zero elements than non-zero elements and the non-zero elements of the frequency coefficients of different regions belong to the same frequency bins;
estimating the vital signs of the person from the frequency coefficients of photoplethysmographic waveforms determined for different regions; and
rendering the vital signs of the person to a controller of a vehicle configured to execute a control action based on the estimated vital signs of the person driving the vehicle.

20. A remote photoplethysmography (RPPG) system, comprising: a processor; and memory having instructions stored thereon that, when executed by the processor, cause the RPPG system to:
receive a sequence of measurements of intensities of different regions of a skin of a person indicative of vital signs of the person;
solve an optimization problem to determine frequency coefficients of photoplethysmographic waveforms corresponding to the measured intensities at each of the different regions to reduce a difference between intensities of the skin of different regions reconstructed from the frequency coefficients of corresponding regions and the corresponding measured intensities of the skin while enforcing joint sparsity on the frequency coefficients of different regions, wherein the joint sparsity is enforced on the optimization problem as a constraint specifying that the frequency coefficients of each region have more zero elements than non-zero elements and the non-zero elements of frequency coefficients of different regions belong to the same frequency bins;
estimate the vital signs of the person from the frequency coefficients of photoplethysmographic waveforms determined for different regions; and
submit the estimated vital signs to a controller of a vehicle configured to execute a control action based on the estimated vital signs of the person driving the vehicle.

* * * * *